United States Patent
Elomari et al.

(10) Patent No.: US 9,056,779 B2
(45) Date of Patent: Jun. 16, 2015

(54) METHOD FOR PREPARING MWW-TYPE MOLECULAR SIEVES

(71) Applicants: Saleh Ali Elomari, Fairfield, CA (US); Timi Pravin Singa, San Francisco, CA (US)

(72) Inventors: Saleh Ali Elomari, Fairfield, CA (US); Timi Pravin Singa, San Francisco, CA (US)

(73) Assignee: Chevron U.S.A. Inc., San Ramon, CA (US)

(*) Notice: Subject to any disclaimer, the term of this patent is extended or adjusted under 35 U.S.C. 154(b) by 160 days.

(21) Appl. No.: 14/030,748

(22) Filed: Sep. 18, 2013

(65) Prior Publication Data

US 2015/0078993 A1    Mar. 19, 2015

(51) Int. Cl.
| | | |
|---|---|---|
| *C01B 33/36* | (2006.01) | |
| *C01B 39/00* | (2006.01) | |
| *C01B 39/48* | (2006.01) | |
| *B01J 29/70* | (2006.01) | |
| *C07C 2/12* | (2006.01) | |
| *C01B 37/02* | (2006.01) | |
| *B01J 29/85* | (2006.01) | |

(52) U.S. Cl.
CPC .............. *C01B 39/48* (2013.01); *B01J 29/70* (2013.01); *C07C 2/12* (2013.01); *C01B 37/02* (2013.01); *B01J 29/85* (2013.01)

(58) Field of Classification Search
CPC .......... C01B 39/48; C01B 37/02; B01J 29/70; B01J 29/85; C07C 2/12
USPC .......................................................... 423/704
See application file for complete search history.

(56) References Cited

U.S. PATENT DOCUMENTS

| 5,202,014 A | 4/1993 | Zones et al. |
| 7,883,686 B2 | 2/2011 | Lai et al. |
| 2010/0260665 A1* | 10/2010 | Archer et al. ................ 423/706 |
| 2012/0114553 A1 | 5/2012 | Zones et al. |
| 2014/0356280 A1* | 12/2014 | Ouyang et al. ............... 423/713 |

FOREIGN PATENT DOCUMENTS

WO    WO2010/118377    *    4/2010   ............. C01B 39/48

OTHER PUBLICATIONS

Jones et al, "A novel approach to borosilicate zeolite synthesis in the presence of fluoride", Microporous and Mesoporous Materials 146 (2011) 48-56.*
PCT/US2014/055993, Notification of Transmittal of The International Search Report and The Written Opinion of The International Searching Authority, or The Declaration, mail date Jan. 21, 2015, 14 pages.

* cited by examiner

*Primary Examiner* — Bijay Saha
(74) *Attorney, Agent, or Firm* — Michael D. Ross

(57) ABSTRACT

The present invention is directed to a process for preparing MWW-type molecular sieves using 1,3-diisobutylimidazolium as a structure directing agent.

11 Claims, No Drawings

METHOD FOR PREPARING MWW-TYPE MOLECULAR SIEVES

FIELD OF THE INVENTION

The present invention is directed to a process for preparing MWW-type molecular sieves using 1,3-diisobutylimidazolium as a structure directing agent.

BACKGROUND OF THE INVENTION

Zeolites are a class of important materials used in the chemical industry for processes such as gas stream purification and hydrocarbon conversion processes. Zeolites are porous solids having interconnected pores of different sizes. Zeolites typically have a one-, two- or three-dimensional crystalline pore structure having pores of one or more molecular dimensions that selectively adsorb molecules that can enter the pores, and exclude those molecules that are too large. The pore size, pore shape, interstitial spacing or channels, composition, crystal morphology and structure are a few characteristics of zeolites that determine their use in various adsorption and hydrocarbon conversion processes.

Molecular sieves identified by the International Zeolite Associate (IZA) as having the structure code MWW are known. For example, the molecular sieve known as SSZ-25 is a known crystalline MWW material. It is disclosed in U.S. Pat. No. 5,202,014, issued Apr. 13, 1993 to Zones et al. In that patent, the SSZ-25 molecular sieve is prepared using a adamantane quaternary ammonium hydroxide (e.g. N,N,N-trimethyl-1-adamantanammonium hydroxide) as the structure-directing agent (SDA).

U.S. Pat. No. 4,954,325 to Chu and Rubin, published Sep. 4, 1990, discloses the preparation of MWW molecular sieve MCM-22 using hexamethyleneimine. Other known SDAs for synthesizing MCM-22 include N,N,N,N'N'N'-hexamethyl-1,5-hexanediaminium salts, N,N,N,N'N'N'-hexamethyl-1,5-pentanediaminium salts, cyclopentylamine-based SDAs, cyclohexylamine-based SDAs, cycloheptylamine-based SDAs, heptamethyleneimine-based SDAs, and homopiperazine-based SDAs, as described in U.S. Pat. No. 7,842,277 to Roth et al., issued Nov. 30, 2010, and U.S. Pat. No. 7,883,686 to Lai et al., issued Feb. 8, 2011.

However, known SDAs useful for making MWW materials are complex and typically not available in quantities necessary to produce MWW materials on a commercial scale. It has now been found that MWW-type molecular sieves can be prepared using cationic 1,3-diisobutylimidazolium as the structure directing agent.

SUMMARY OF THE INVENTION

In accordance with the present invention there is provided a method for preparing MWW-type molecular sieves by contacting under crystallization conditions: (1) at least one source of at least one oxide of a tetravalent element; (2) optionally, one or more sources of one or more oxides selected from the group consisting of oxides of trivalent elements, pentavalent elements, and mixtures thereof; (3) at least one source of an element selected from Groups 1 and 2 of the Periodic Table; (4) hydroxide ions; and (5) cationic 1,3-diisobutylimidazolium as the structure directing agent.

The present invention also includes a process for preparing a MWW-type molecular sieve by:

(a) preparing a reaction mixture containing: (1) at least one source of at least one oxide of a tetravalent element; (2) optionally, one or more sources of one or more oxides selected from the group consisting of oxides of trivalent elements, pentavalent elements, and mixtures thereof; (3) at least one source of an element selected from Groups 1 and 2 of the Periodic Table; (4) hydroxide ions; (5) cationic 1,3-diisobutylimidazolium as the structure directing agent; and (6) water; and (b) subjecting the reaction mixture to crystallization conditions sufficient to form crystals of the MWW-type molecular sieve.

Where the molecular sieve formed is an intermediate material, the process of the present invention includes a further post-crystallization processing in order to achieve the target molecular sieve (e.g. by post-synthesis heteroatom lattice substitution or acid leaching).

The present invention also provides a MWW-type molecular sieve having a composition, as-synthesized and in the anhydrous state, in terms of mole ratios, as follows:

|  | Broadest | Secondary |
|---|---|---|
| $TO_2/X_2O_b$ | 10-1000 | 20-100 |
| $Q/TO_2$ | 0.05-1 | 0.10-0.3 |
| $M/TO_2$ | 0.01-1.0 | 0.05-0.5 | wherein:

(1) T is selected from the group consisting of tetravalent elements from Groups 4-14 of the Periodic Table, and mixtures thereof;

(2) X is selected from the group consisting of trivalent and pentavalent elements from Groups 3-13 of the Periodic Table, and mixtures thereof;

(3) stoichiometric variable b equals the valence state of compositional variable X (e.g. when X is trivalent, b=3; when X is pentavalent, b=5);

(4) M is selected from the group consisting of elements from Groups 1 and 2 of the Periodic Table; and (5) Q is cationic 1,3-diisobutylimidazolium.

DETAILED DESCRIPTION OF THE INVENTION

Introduction

The term "Periodic Table" refers to the version of IUPAC Periodic Table of the Elements dated Jun. 22, 2007, and the numbering scheme for the Periodic Table Groups is as described in Chemical and Engineering News, 63(5), 27 (1985).

The term "molecular sieve" includes (a) intermediate and (b) final or target molecular sieves and zeolites produced by (1) direct synthesis or (2) post-crystallization treatment (secondary synthesis). Secondary synthesis techniques allow for the synthesis of a target material from an intermediate material by heteroatom lattice substitution or other techniques. For example, an aluminosilicate can be synthesized from an intermediate borosilicate by post-crystallization heteroatom lattice substitution of the Al for B. Such techniques are known, for example as described in U.S. Pat. No. 6,790,433 to C. Y. Chen and Stacey Zones, issued Sep. 14, 2004.

The term "MWW-type molecular sieve" includes all molecular sieves and their isotypes that have been assigned the International Zeolite Associate framework code MWW, as described in the *Atlas of Zeolite Framework Types*, eds. Ch. Baerlocher, L. B. McCusker and D. H. Olson, Elsevier, 6$^{th}$ revised edition, 2007. The zeolitic materials designated by the Structure Commission of the International Zeolite Association as being of the MWW topology are multi-layered materials which have two pore systems arising from the presence of both 10 and 12 membered rings. The *Atlas of Zeolite Framework Types* (citation herein below) classes five differently named materials as having this same topology: SSZ-25, ERB-I, ITQ-I, PSH-3, and MCM-22.

It will be understood by a person skilled in the art that the MWW-type molecular sieve materials made according to the process described herein may contain impurities, such as amorphous materials; unit cells having non-MWW framework topologies (e.g., MFI, MTW); and/or other impurities (e.g., heavy metals and/or organic hydrocarbons).

Where permitted, all publications, patents and patent applications cited in this application are herein incorporated by reference in their entirety; to the extent such disclosure is not inconsistent with the present invention.

Unless otherwise specified, the recitation of a genus of elements, materials or other components, from which an individual component or mixture of components can be selected, is intended to include all possible sub-generic combinations of the listed components and mixtures thereof. Also, "include" and its variants are intended to be non-limiting, such that recitation of items in a list is not to the exclusion of other like items that may also be useful in the materials, compositions and methods of this invention.

The present invention is directed to a method of making MWW-type molecular sieves using a 1,3-diisobutylimidazolium structure directing agent (SDA), represented by structure (1) below.

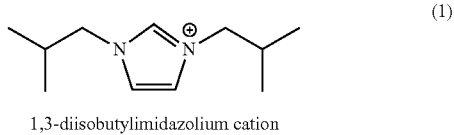

1,3-diisobutylimidazolium cation

Reaction Mixture

In general, the MWW-type molecular sieve is prepared by:

(a) preparing a reaction mixture containing: (1) at least one source of at least one oxide of a tetravalent element; (2) optionally, one or more sources of one or more oxides selected from the group consisting of oxides of trivalent elements, pentavalent elements, and mixtures thereof; (3) at least one source of an element selected from Groups 1 and 2 of the Periodic Table; (4) hydroxide ions; (5) cationic 1,3-diisobutylimidazolium as the structure directing agent; and (6) water; and (b) subjecting the reaction mixture to crystallization conditions sufficient to form crystals of the MWW-type molecular sieve.

Where the molecular sieve formed is an intermediate material, the process of the present invention includes a further step of synthesizing a target molecular sieve by post-synthesis techniques, such as heteroatom lattice substitution techniques and acid leaching.

The composition of the reaction mixture from which the MWW-type molecular sieve is formed, in terms of molar ratios, is identified in Table 1 below:

TABLE 1

| Reactants | Broadest | Secondary |
|---|---|---|
| $TO_2/X_2O_b$ | 10-1000 | 15-80 |
| $M/TO_2$ | 0.01-1.0 | 0.05-0.5 |
| $Q/TO_2$ | 0.05-1 | 0.1-0.3 |

TABLE 1-continued

| Reactants | Broadest | Secondary |
|---|---|---|
| $OH^-/TO_2$ | 0.1-1.0 | 0.05-0.5 |
| $H_2O/TO_2$ | 5-100 | 15-50 | wherein compositional variables T, X, M and Q are as described herein above.

In one subembodiment, the composition of the reaction mixture from which the MWW-type molecular sieve is formed, in terms of molar ratios, is identified in Table 2 below:

TABLE 2

| Reactants | Broadest | Secondary |
|---|---|---|
| $SiO_2/Al_2O_3$ | 15-300 | 20-80 |
| $M/SiO_2$ | 0.01-0.5 | 0.05-0.3 |
| $Q/SiO_2$ | 0.05-1.0 | 0.1-0.3 |
| $OH^-/SiO_2$ | 0.1-1.0 | 0.10-0.40 |
| $H_2O/SiO_2$ | 10-100 | 20-40 |

As noted above, for each embodiment described herein, T is selected from the group consisting of elements from Groups 4-14 of the Periodic Table. In one subembodiment, T is selected from the group consisting of germanium (Ge), silicon (Si), titanium (Ti), and mixtures thereof. In another subembodiment, T is selected from the group consisting of germanium (Ge), silicon (Si), and mixtures thereof. In one subembodiment, T is Si. Sources of elements selected for composition variable T include oxides, hydroxides, acetates, oxalates, ammonium salts and sulfates of the element(s) selected for T and X. In one subembodiment, each source of the element(s) selected for composition variable T is an oxide. Where T is Si, sources useful herein for Si include fumed silica, precipitated silicates, silica hydrogel, silicic acid, colloidal silica, tetra-alkyl orthosilicates (e.g. tetraethyl orthosilicate), and silica hydroxides. Examples of silica sources useful for making high-silica forms of the MWW-type molecular sieve include fumed silica (e.g. CAB-O-SIL M-5, Cabot Corporation) and hydrated silica (e.g. HI-SIL 233, PPG Industries), and mixtures thereof. Also useful are colloidal silicas where the solid content is 30-40 wt. % $SiO_2$, and these material may be stabilized by small amounts of sodium or ammonium cations. Further, colloidal sols where aluminum is dispersed in the silica sol can be used to provide an instant $SiO_2/Al_2O_3$ ratio which is desired. Sources useful herein for Ge include germanium oxide and germanium ethoxide.

For each embodiment described herein, X is selected from the group consisting of elements from Groups 3-13 of the Periodic Table. In one subembodiment, X is selected from the group consisting of gallium (Ga), aluminum (Al), iron (Fe), boron (B), indium (In), and mixtures thereof. In another subembodiment, X is selected from the group consisting of Al, B, Fe, Ga, and mixtures thereof. In another subembodiment, X is selected from the group consisting of Al, Fe, Ga, and mixtures thereof. Sources of elements selected for optional composition variable X include oxides, hydroxides, acetates, oxalates, ammonium salts and sulfates of the element(s) selected for X. Typical sources of aluminum oxide include aluminates, alumina, and aluminum compounds such as $AlCl_3$, $Al_2(SO_4)_3$, aluminum hydroxide ($Al(OH)_3$), kaolin clays, and other zeolites. An example of the source of aluminum oxide is LZ-210 zeolite (a type of Y zeolite). Boron, gallium, and iron can be added in forms corresponding to their aluminum and silicon counterparts.

As described herein above, for each embodiment described herein, the reaction mixture may be formed using at least one source of an element selected from Groups 1 and 2 of the Periodic Table (referred to herein as M). In one subembodiment, the reaction mixture is formed using a source of an element from Group 1 of the Periodic Table. In another subembodiment, the reaction mixture is formed using a source of sodium (Na). Any M-containing compound which is not detrimental to the crystallization process is suitable. Sources for such Groups 1 and 2 elements include oxides, hydroxides, nitrates, sulfates, halides, oxalates, citrates and acetates thereof.

The SDA cation is typically associated with anions ($X^-$) which may be any anion that is not detrimental to the formation of the zeolite. Representative anions include elements from Group 17 of the Periodic Table (e.g., fluoride, chloride, bromide and iodide), hydroxide, acetate, sulfate, tetrafluoroborate, carboxylate, and the like.

The reaction mixture can be prepared either batch wise or continuously. Crystal size, morphology and crystallization time of the molecular sieve described herein may vary with the nature of the reaction mixture and the crystallization conditions.

Crystallization and Post-Synthesis Treatment

In practice, the molecular sieve is prepared by:

(a) preparing a reaction mixture as described herein above; and (b) maintaining the reaction mixture under crystallization conditions sufficient to form the molecular sieve. (See, Harry Robson, *Verified Syntheses of Zeolitic Materials*, $2^{nd}$ revised edition, Elsevier, Amsterdam (2001)).

The reaction mixture is maintained at an elevated temperature until the molecular sieve is formed. The hydrothermal crystallization is usually conducted under pressure, and usually in an autoclave so that the reaction mixture is subject to autogenous pressure, at a temperature between 130° C. and 200° C., for a period of one to six days.

The reaction mixture may be subjected to mild stirring or agitation during the crystallization step. It will be understood by a person skilled in the art that the molecular sieves described herein may contain impurities, such as amorphous materials, unit cells having framework topologies which do not coincide with the molecular sieve, and/or other impurities (e.g., organic hydrocarbons).

During the hydrothermal crystallization step, the molecular sieve crystals can be allowed to nucleate spontaneously from the reaction mixture. The use of crystals of the molecular sieve as seed material can be advantageous in decreasing the time necessary for complete crystallization to occur. In addition, seeding can lead to an increased purity of the product obtained by promoting the nucleation and/or formation of the molecular sieve over any undesired phases. When used as seeds, seed crystals are added in an amount between 1% and 10% of the weight of the source for compositional variable T used in the reaction mixture.

Once the molecular sieve crystals have formed, the solid product is separated from the reaction mixture by standard mechanical separation techniques such as filtration. The crystals are water-washed and then dried to obtain the as-synthesized molecular sieve crystals. The drying step can be performed at atmospheric pressure or under vacuum.

The molecular sieve can be used as-synthesized, but typically will be thermally treated (calcined). The term "as-synthesized" refers to the molecular sieve in its form after crystallization, prior to removal of the SDA. The SDA can be removed by thermal treatment (e.g., calcination), preferably in an oxidative atmosphere (e.g., air, gas with an oxygen partial pressure of greater than 0 kPa) at a temperature readily determinable by one skilled in the art sufficient to remove the SDA from the molecular sieve. The SDA can also be removed by photolysis techniques (e.g. exposing the SDA-containing molecular sieve product to light or electromagnetic radiation that has a wavelength shorter than visible light under conditions sufficient to selectively remove the organic compound from the molecular sieve) as described in U.S. Pat. No. 6,960,327 to Navrotsky and Parikh, issued Nov. 1, 2005.

The molecular sieve can subsequently be calcined in steam, air or inert gas at temperatures ranging from about 200° C. to about 800° C. for periods of time ranging from 1 to 48 hours, or more. Usually, it is desirable to remove the extra-framework cation (e.g. $H^+$) by ion-exchange or other known method and replace it with hydrogen, ammonium, or any desired metal-ion.

Where the molecular sieve formed is an intermediate material, the target molecular sieve can be achieved using post-synthesis techniques such as heteroatom lattice substitution techniques. The target MWW molecular sieve can also be achieved by removing heteroatoms from the lattice by known techniques such as acid leaching.

The molecular sieve made from the process of the present invention can be formed into a wide variety of physical shapes. Generally speaking, the molecular sieve can be in the form of a powder, a granule, or a molded product, such as extrudate having a particle size sufficient to pass through a 2-mesh (Tyler) screen and be retained on a 400-mesh (Tyler) screen. In cases where the catalyst is molded, such as by extrusion with an organic binder, the molecular sieve can be extruded before drying, or, dried or partially dried and then extruded.

The molecular sieve can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. No. 4,910,006, issued May 20, 1990 to Zones et al., and U.S. Pat. No. 5,316,753, issued May 31, 1994 to Nakagawa.

Characterization of the Molecular Sieve

The MWW-type molecular sieves made by the process of the present invention have a composition, as-synthesized and in the anhydrous state, as described in Table 3 (in terms of mole ratios), wherein compositional variables T, X, M and Q are as described herein above.

TABLE 3

|  | Broadest | Secondary |
|---|---|---|
| $TO_2/X_2O_b$ | 10-1000 | 20-100 |
| $Q/TO_2$ | 0.05-1 | 0.10-0.3 |
| $M/TO_2$ | 0.01-1.0 | 0.05-0.5 |

In one subembodiment, the MWW-type molecular sieves made by the process of the present invention have a composition, as-synthesized and in the anhydrous state, as described in Table 4 (in terms of mole ratios), wherein compositional variables M and Q are as described herein above.

TABLE 4

|  | Broadest | Secondary |
|---|---|---|
| $SiO_2/Al_2O_3$ | 15-300 | 20-80 |
| $Q/SiO_2$ | 0.05-1.0 | 0.1-0.3 |
| $M/SiO_2$ | 0.01-0.05 | 0.05-0.3 |

The MWW-type molecular sieves synthesized by the process of the present invention are characterized by their X-ray diffraction pattern (XRD). X-ray diffraction patterns representative of MWW-type molecular sieves can be referenced in M. M. J. Treacy et al., *Collection of Simulated XRD Powder Patterns for Zeolites,* 5th Revised Edition, 2007 of the International Zeolite Association. Minor variations in the diffraction pattern can result from variations in the mole ratios of the framework species of the particular sample due to changes in lattice constants. In addition, sufficiently small crystals will affect the shape and intensity of peaks, leading to significant peak broadening. Minor variations in the diffraction pattern can also result from variations in the organic compound used in the preparation and from variations in the T/X (e.g. Si/Al) mole ratio from sample to sample. Calcination can also cause minor shifts in the X-ray diffraction pattern. Notwithstanding these minor perturbations, the basic crystal lattice structure remains unchanged.

The powder X-ray diffraction patterns presented herein were collected by standard techniques. The radiation was CuK-α radiation. The peak heights and the positions, as a function of 2θ where θ is the Bragg angle, were read from the relative intensities of the peaks, and d, the interplanar spacing in Angstroms corresponding to the recorded lines, can be calculated.

EXAMPLES

The following examples demonstrate but do not limit the present invention.

Example 1

Synthesis of 1,3-diisobutylimidazolium Hydroxide 1,3-diisobutylimidazolium bromide was made according to the following procedure. In a 3-neck reaction flask, imidazole (1 molar equivalent), potassium bicarbonate (1.25 molar equivalent), and 1-bromo-2-methylpropane (3 molar equivalent) were all mixed in methanol (enough methanol to make 0.5M with respect to imidazole). The resulting solution was stirred while heating at reflux for 96 hours. An additional ½ equivalent of the bromide was added and the reaction was left to further stir at room temperature for an additional 48 hours. The reaction progression was monitored by NMR analysis.

Once complete, the reaction mixture (solids and solution) was concentrated using a rotary evaporator at reduced pressure to remove methanol (the solvent). Then, the resulting solids were rinsed with twice with diethyl ether (100 ml ether/1 mole product) to rinse off excess bromides. The ether-rinsed solids were dissolved in chloroform (300 ml chloroform/mol product). The desired products dissolve in chloroform leaving behind the undesired inorganic salts. The mixture is then filtered through a fritted funnel glass. The filtrate is collected and concentrated on a rotary evaporator at reduced pressure in hot water bath (50° C.). The obtained solids after removing the chloroform, off-white solids, were dissolved in a minimum amount of isopropyl alcohol and then precipitated by adding diethyl ether. The precipitate was filtered out and dried on a rotary evaporator at reduced pressure and while in hot bath at 70° C. The reaction afforded the desired and white powdery material in 87% yield.

The 1,3-diisobutylimidazolium bromide product was dissolved in deionized water (10 mL water/1 mmol salt) in a polyethylene plastic bottle. To the solution, Bio-Rad AG 1-X8 ion-exchange resin (1.1 g resin/mmol salt) was added and the slurry-like mixture was gently stirred overnight. The exchange solution was filtered and a small aliquot of the filtrate was titrated with 0.1N HCl to indicate the exchange yielded 89% of the desired 1,3-diisobutylimidazolium hydroxide product.

Example 2

In a 23 cc Teflon liner, 2 mmol of 1,3-diisobutylimidazolium hydroxide and 1.5 mmol of NaOH in 10 gram of water were mixed with 0.8 g of CAB-O-SIL M5 fumed silica and 0.25 g of LZ-Y52 Y zeolite (Na—Y). The mixture was thoroughly mixed and stirred to give a thin gel solution. The Teflon liner was capped off and placed in an autoclave and affixed to a rotating spit (~43 rpm) in an oven and heated at ~160° C. The progress was checked at intervals of 5 days by scanning electron microscopy and by monitoring the pH of the gel. The crystallization was complete in 15 days to give solution and solids. The reaction mixture was filtered and the solids were separated, washed thoroughly with deionized water and air dried overnight. The solids were further dried in an oven at 125° C. for 2 hours. The reaction yielded a 0.80 g of MWW-type zeolite, as confirmed by powder XRD spectroscopy.

The as-made sample was calcined in air in a muffle furnace oven from room temperature to 120° C. at a rate of 1° C./minute and held at 120° C. for 2 hours. The temperature was then ramped up to 540° C. at a rate of 1° C./minute. The sample was held at 540° C. for 5 hrs. The temperature was increased at the same rate (1° C./minute) to 595° C. and held there for 5 hrs. Upon calcination, there was a weight loss ranging from 18-20%.

The calcined product of was subjected to a surface area and micropore analysis using nitrogen as adsorbate and via the BET method. The BET surface area of the zeolite was 534.3 $m^2/g$, external surface area of 100 $m^2/g$ with a micropore volume of 0.20 cc/g.

Example 3

Example 2 was repeated, with the exception of the addition of 0.04 g of the as-made zeolite from example 1 to the reaction mixture. The crystallization was complete in 8 days to give 0.85 g of MWW-type zeolite, as confirmed by powder XRD spectroscopy.

Example 4

Example 2 was repeated, with the exception the LZ-Y52 Y zeolite was replaced with 0.035 g Reheis F-2000 alumina as the aluminum source. The reaction was heated at 170° C. for 16 days to give 0.82 g of MWW-type zeolite, as confirmed by powder XRD spectroscopy.

Example 5

Example 4 was repeated, with the exception of the addition of 0.04 g of the as-made zeolite from Example 4 to the reaction mixture. The crystallization was complete in 10 days to give 0.86 g of MCM-22 type zeolite, as confirmed by powder XRD spectroscopy.

What is claimed is:

1. A method for preparing a MWW-type molecular sieve, comprising:
   (a) preparing a reaction mixture containing: (1) at least one source of at least one oxide of a tetravalent element; (2) optionally, one or more sources of one or more oxides selected from the group consisting of oxides of trivalent elements, pentavalent elements, and mixtures thereof; (3) at least one source of an element selected from Groups 1 and 2 of the Periodic Table; (4) hydroxide ions; (5) cationic 1,3-diisobutylimidazolium as a structure directing agent; and (6) water; and
   (b) subjecting the reaction mixture to crystallization conditions sufficient to form crystals of the MWW-type molecular sieve.

2. The method of claim 1, wherein the MWW-type molecular sieve is prepared from a reaction mixture comprising, in terms of mole ratios, the following:

| | |
|---|---|
| $TO_2/X_2O_b$ | 10-1000 |
| $M/TO_2$ | 0.01-1.0 |
| $Q/TO_2$ | 0.05-1 |
| $OH^-/TO_2$ | 0.1-1.0 |
| $H_2O/TO_2$ | 5-100 | wherein:
   (1) T is selected from the group consisting of tetravalent elements from Groups 4-14 of the Periodic Table, and mixtures thereof;
   (2) X is selected from the group consisting of trivalent and pentavalent elements from Groups 3-13 of the Periodic Table, and mixtures thereof;
   (3) stoichiometric variable b equals the valence state of compositional variable X;
   (4) M is selected from the group consisting of elements from Groups 1 and 2 of the Periodic Table; and
   (5) Q is cationic 1,3-diisobutylimidazolium.

3. The method of claim 2, wherein the MWW-type molecular sieve is prepared from a reaction mixture comprising, in terms of mole ratios, the following:

| | |
|---|---|
| $TO_2/X_2O_b$ | 15-80 |
| $M/TO_2$ | 0.05-0.5 |
| $Q/TO_2$ | 0.1-0.3 |
| $OH^-/TO_2$ | 0.05-0.5 |
| $H_2O/TO_2$ | 15-50. |

4. The method of claim 2, wherein the MWW-type molecular sieve has a composition, as made and in an anhydrous state, comprising, in terms of mole ratios, the following:

| | |
|---|---|
| $TO_2/X_2O_b$ | 10-1000 |
| $Q/TO_2$ | 0.05-1 |
| $M/TO_2$ | 0.01-1.0. |

5. The method of claim 1, wherein the MWW-type molecular sieve is prepared from a reaction mixture comprising, in terms of mole ratios, the following:

| | |
|---|---|
| $SiO_2/Al_2O_3$ | 15-300 |
| $M/SiO_2$ | 0.01-0.5 |
| $Q/SiO_2$ | 0.05-1.0 |
| $OH^-/SiO_2$ | 0.1-1.0 |
| $H_2O/SiO_2$ | 10-100 | wherein:
   (1) M is selected from the group consisting of elements from Groups 1 and 2 of the Periodic Table; and
   (2) Q is cationic 1,3-diisobutylimidazolium.

6. The method of claim 5, wherein the MWW-type molecular sieve is prepared from a reaction mixture comprising, in terms of mole ratios, the following:

| | |
|---|---|
| $SiO_2/Al_2O_3$ | 20-80 |
| $M/SiO_2$ | 0.05-0.3 |
| $Q/SiO_2$ | 0.1-0.3 |
| $OH^-/SiO_2$ | 0.10-0.40 |
| $H_2O/SiO_2$ | 20-40. |

7. The method of claim 5, wherein the MWW-type molecular sieve has a composition, as made and in an anhydrous state, comprising, in terms of mole ratios, the following:

| | |
|---|---|
| $SiO_2/Al_2O_3$ | 15-300 |
| $Q/SiO_2$ | 0.05-1.0 |
| $M/SiO_2$ | 0.01-0.05. |

8. The method of claim 1, wherein the MWW-type molecular sieve has a composition, as made and in an anhydrous state, comprising, in terms of mole ratios, the following:

| | |
|---|---|
| $TO_2/X_2O_b$ | 10-1000 |
| $Q/TO_2$ | 0.05-0 1 |
| $M/TO_2$ | 0.01-1.0 | wherein:
   (1) T is selected from the group consisting of tetravalent elements from Groups 4-14 of the Periodic Table, and mixtures thereof;
   (2) X is selected from the group consisting of trivalent and pentavalent elements from Groups 3-13 of the Periodic Table, and mixtures thereof;
   (3) stoichiometric variable b equals the valence state of compositional variable X;
   (4) M is selected from the group consisting of elements from Groups 1 and 2 of the Periodic Table; and
   (5) Q is cationic 1,3-diisobutylimidazolium.

9. The method of claim 8, wherein the MWW-type molecular sieve has a composition, as made and in an anhydrous state, comprising, in terms of mole ratios, the following:

| | |
|---|---|
| $TO_2/X_2O_b$ | 20-100 |
| $Q/TO_2$ | 0.10-0.3 |
| $M/TO_2$ | 0.05-0.5. |

10. The method of claim 1, wherein the MWW-type molecular sieve has a composition, as made and in an anhydrous state, comprising, in terms of mole ratios, the following:

| | |
|---|---|
| $SiO_2/Al_2O_3$ | 15-300 |
| $Q/SiO_2$ | 0.05-1.0 |
| $M/SiO_2$ | 0.01-0.05 | wherein:
 (1) M is selected from the group consisting of elements from Groups 1 and 2 of the Periodic Table; and
 (2) Q is cationic 1,3-diisobutylimidazolium.

11. The method of claim 10, wherein the MWW-type molecular sieve has a composition, as made and in the anhydrous state, comprising, in terms of mole ratios, the following:

| | |
|---|---|
| $SiO_2/Al_2O_3$ | 20-80 |
| $Q/SiO_2$ | 0.1-0.3 |
| $M/SiO_2$ | 0.05-0.3. |

(1) M is selected from the group consisting of elements from Groups 1 and 2 of the Periodic Table; and
 (2) Q is cationic 1,3-diisobutylimidazolium.

* * * * *